(12) United States Patent
Ueda et al.

(10) Patent No.: US 9,070,531 B2
(45) Date of Patent: Jun. 30, 2015

(54) X-RAY GENERATOR TUBE HAVING IMPROVED COOLING CONTAINER AND X-RAY IMAGING APPARATUS INCLUDING THE SAME

(75) Inventors: Kazuyuki Ueda, Tokyo (JP); Miki Tamura, Kawasaki (JP); Yoshihiro Yanagisawa, Fujisawa (JP); Yasue Sato, Machida (JP); Koji Yamazaki, Ayase (JP); Takao Ogura, Yokohama (JP); Shuji Aoki, Yokohama (JP); Ichiro Nomura, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/111,512

(22) PCT Filed: Apr. 6, 2012

(86) PCT No.: PCT/JP2012/002426
§ 371 (c)(1),
(2), (4) Date: Oct. 11, 2013

(87) PCT Pub. No.: WO2012/140860
PCT Pub. Date: Oct. 18, 2012

(65) Prior Publication Data
US 2014/0029725 A1    Jan. 30, 2014

(30) Foreign Application Priority Data

Apr. 13, 2011   (JP) ................................ 2011-088806

(51) Int. Cl.
*H01J 35/12* (2006.01)
*H01J 35/02* (2006.01)
*H05G 1/04* (2006.01)
*H05G 1/02* (2006.01)
*H01J 35/16* (2006.01)
*A61B 6/00* (2006.01)

(52) U.S. Cl.
CPC ................ *H01J 35/16* (2013.01); *H01J 35/12* (2013.01); *A61B 6/4488* (2013.01); *H01J 2235/186* (2013.01); *H05G 1/025* (2013.01); *H05G 1/04* (2013.01)

(58) Field of Classification Search
CPC ............ H01J 35/12; H01J 35/02; H05G 1/04; H05G 1/02; A61B 6/4488
USPC ......... 378/119, 121, 137, 138, 141, 142, 193, 378/199, 200, 204, 210
See application file for complete search history.

(56) References Cited

U.S. PATENT DOCUMENTS

| | | | |
|---|---|---|---|
| 4,767,961 A | 8/1988 | Koller et al. | |
| 2009/0010393 A1 | 1/2009 | Klinkowstein et al. | |
| 2013/0016811 A1* | 1/2013 | Ueda et al. ...................... | 378/62 |

FOREIGN PATENT DOCUMENTS

| | | |
|---|---|---|
| JP | S31-014523 Y | 9/1956 |
| JP | 61066399 A | 4/1986 |
| JP | 2002025792 A | 1/2002 |
| JP | 2005-116534 A | 4/2005 |
| JP | 2007066655 A | 3/2007 |

* cited by examiner

*Primary Examiner* — Anastasia Midkiff
(74) *Attorney, Agent, or Firm* — Canon USA Inc. IP Division

(57) ABSTRACT

Provided is an X-ray generator comprising an X-ray tube including a cylindrical body; an electron source in the body; a target at an end of the X-ray tube facing the electron source, the target generating X-rays by irradiation with electrons; a container in which the X-ray tube is arranged; insulating liquid filled between the X-ray tube and the container; and a holding member holding the body of the X-ray tube in the container, with a channel for the insulating liquid around the X-ray tube. The distance between the holding member and the end face at the end of the body in the direction in which the electron source and the target face is twice or more as large as the minimum width of the channel that is in contact with the outer surface of the X-ray tube at the end face side with respect to the holding member. This allows heat in the target to be quickly radiated, thus allowing X-rays to be generated stably for a long time.

10 Claims, 7 Drawing Sheets

X-RAY GENERATOR TUBE HAVING IMPROVED COOLING CONTAINER AND X-RAY IMAGING APPARATUS INCLUDING THE SAME

TECHNICAL FIELD

The present invention relates to X-ray generators and X-ray imaging apparatus, and in particular, to an X-ray generator equipped with a transmission X-ray tube that is held in a container filled with insulating liquid by a holding member, as well as an X-ray imaging apparatus including the same.

BACKGROUND ART

A known X-ray generator that generates X-rays by radiating electrons emitted from an electron source onto a target is equipped with an X-ray tube that accommodates the electron source and the target in its sealed interior. A known example of the electron source disposed in the X-ray tube in the related art is a thermal electron source, such as a filament. Some thermal electron sources are of a small type, such as an impregnated hot-cathode electron-emitting device used as an electron source for a cathode-ray tube. An X-ray tube that uses a thermal electron source accelerates part of a thermal electron flux emitted from the thermal electron source that is heated to high temperature to have high energy through a Wehnelt electrode, an extraction electrode, an accelerating electrode, and a lens electrode. At the same time, after a desired shape of electron flux is formed, the shaped electron flux is radiated onto a target formed of metal, such as tungsten, to generate X-rays.

However, when the electron flux accelerated to have high energy is radiated onto the target to generate X-rays, about 1% or less of the energy of the electrons that collide with the target becomes X-rays, and the remaining about 99% or more becomes heat. At that time, the heat generated in the target is radiated as radiant heat, but the heat radiation is sometimes insufficient because the target is in a vacuum. If the amount of heat radiated is small, the target is increased in temperature. Thus, if a target substrate that supports the target is used, the target substrate sometimes melts, and if no target substrate is used, the target sometimes melts. This requires radiating the heat generated in the target quickly.

Japanese Patent Application Laid-Open No. 2002-025792 discloses a technology for enhancing the effect of radiating the heat generated in the target by placing an X-ray tube in the container, filling electrically insulating oil between the container and the X-ray tube, and transferring the heat to the electrically insulating oil.

CITATION LIST

Patent Literature

PTL 1: Japanese Patent Laid-Open No. 2002-025792

SUMMARY OF INVENTION

Technical Problem

However, with the X-ray generator in which a transmission X-ray tube is held in the container filled with electrically insulating oil by a holding member, the convection of the electrically insulating oil heated by the heat generated in the target is obstructed by the holding member to decrease in flow rate, so that the heat in the target sometimes cannot be quickly radiated. If the heat cannot be quickly radiated, the electrically insulating oil increases in temperature to 60 degrees (Celsius) or higher to form bubbles and be decomposed by heat, which reduces the electrical insulation performance of the electrically insulating oil, causing the possibility of electrical discharge to damage the X-ray tube. The damage to the X-ray tube due to the electrical discharge poses a problem in that X-rays cannot be generated stably for a long time.

The present invention provides a reliable X-ray generator in which a transmission X-ray tube is held in a container filled with insulating liquid by a holding member, in which heat in a target can be quickly radiated, and which can generate X-rays stably for a long time, as well as an X-ray imaging apparatus including the same.

Solution to Problem

To achieve the above object, an X-ray generator according to an aspect of the present invention comprising an X-ray tube including a cylindrical body; an electron source in the body; a target at an end of the body facing the electron source, the target generating X-rays by irradiation with electrons; a container in which the X-ray tube is arranged; insulating liquid filled between the X-ray tube and the container; and a holding member holding the body of the X-ray tube in the container, with a channel for the insulating liquid around the X-ray tube. The distance between the holding member and the end face at the end of the body in the direction in which the electron source and the target face is twice or more as large as the minimum width of the channel that is in contact with the outer surface of the X-ray tube at the end face side with respect to the holding member.

Advantageous Effects of Invention

According to an aspect of the present invention, a transmission X-ray tube placed in a container filled with insulating liquid is held by a holding member, with a channel around the X-ray tube, and the holding member is located a fixed distance apart from a target side surface of the transmission X-ray tube. This provides an X-ray tube holding structure in which the convection of the insulating liquid is not obstructed by the holding member, which enhances the cooling effect of the insulating liquid, thus allowing the heat in the target to be quickly radiated. This can prevent a decrease in the electrical insulation performance of the insulating liquid to reduce the occurrence of electric discharge, thus allowing a reliable X-ray generator capable of generated X-rays stably for a long time and an X-ray imaging apparatus including the same to be achieved.

DESCRIPTION OF EMBODIMENTS

X-ray generators and an X-ray imaging apparatus according to embodiments of the present invention will be described hereinbelow.

First Embodiment

Figure 1A:
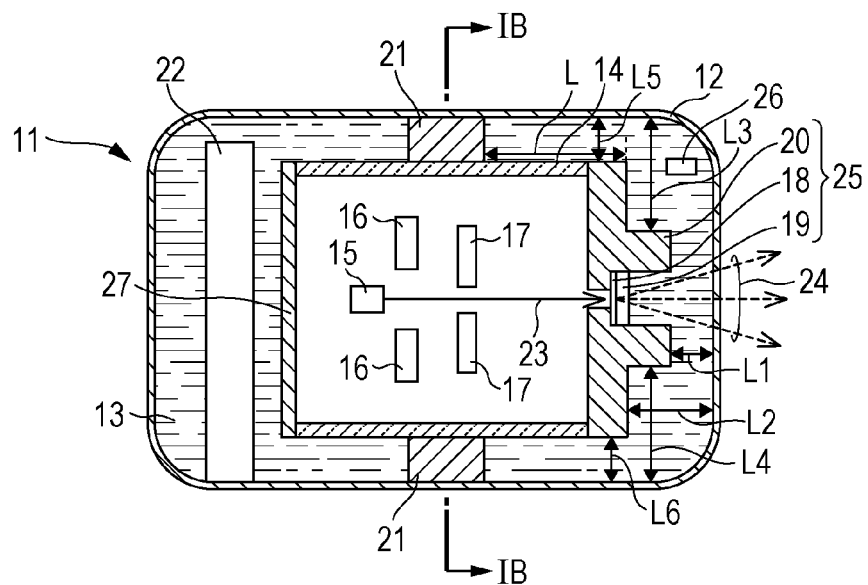
FIG. 1A is a schematic cross-sectional view of an X-ray generator according to a first embodiment of the present invention.
Figure 1B:
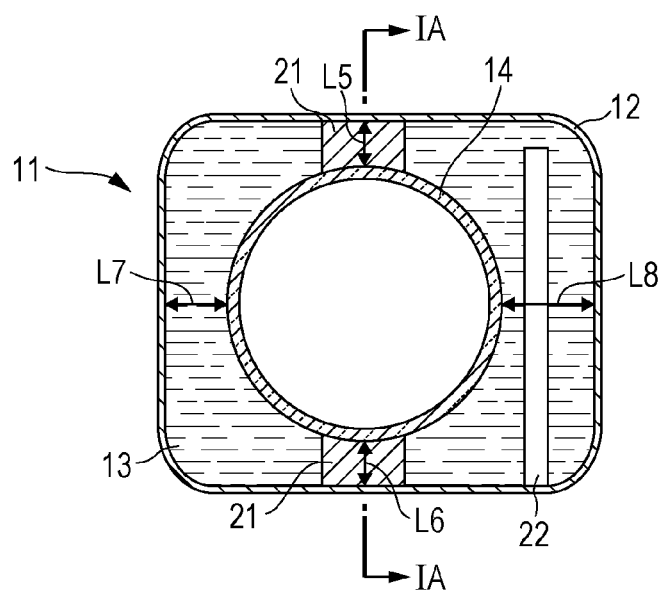
FIG. 1B is a schematic cross-sectional view of the X-ray generator according to the first embodiment.

FIG. 1A is a schematic cross-sectional view of an X-ray generator 11 of a first embodiment of the present invention, taken along a plane including line IA-IA in FIG. 1B. FIG. 1B is a schematic cross-sectional view of the X-ray generator 11 of the first embodiment, taken along a plane including line 1B-1B in FIG. 1A.

A container 12 is a container for accommodating components, such as an X-ray tube 14. The container 12 is filled with insulating liquid 13. The container 12 filled with the insulating liquid 13 accommodates the cylindrical X-ray tube 14 whose body is held by a holding member 21 fixed to the inner surface of the container 12. The periphery of the X-ray tube 14 serves as a (fluid) channel of the insulating liquid 13. The channel is in contact with the outer surface of the X-ray tube 14 and the holding member 21, through which the insulating liquid 13 can circulate around the X-ray tube 14. Examples of the material of the container 12 include metal, such as iron, stainless steel, lead, brass, and copper. The insulating liquid 13 can be injected into the container 12 through an inlet (not shown) provided at part of the container 12. To prevent pressure in the container 12 from increasing when the insulating liquid 13 in the X-ray generator 11 in operation increases in temperature and expands, a pressure regulation opening (not shown) made of an elastic member is provided in part of the container 12 as necessary.

The insulating liquid 13 can have a high electrical insulation performance and high cooling capacity. Furthermore, the insulating liquid 13 can be resistant to deterioration due to heat because the target 18 becomes hot due to heat generation, and the heat is transmitted to the insulating liquid 13, and can have low viscosity from the viewpoint of the ease of flow of the insulating liquid 13. For example, electrically insulating oil and fluorine insulating liquid can be used.

The X-ray tube 14 is a cylindrical container whose both ends are closed so that the interior is sealed. An electron source 15 is disposed in the cylindrical body. A target 18 is provided at an end of the cylinder opposing the electron source 15. The target 18 serves as an X-ray extraction window of the transmission X-ray tube 14. Electrons emitted from the electron source 15 irradiate the target 18, where X-rays are generated, and the generated X-rays are discharged outwards through the X-ray extraction window. Although the X-ray tube 14 of the first embodiment is configured such that one end of the cylinder is closed by a target-side wall 25 formed of the target 18, a target substrate 19, and a shielding member 20, and the other end of the cylinder is closed by an electron-source-side wall 27, it is not limited thereto. The shape of the X-ray tube 14 may be rectangular cylinder or the like. To keep the degree of vacuum of the interior at $1*10^{-4}$ Pa or lower at which the electron source 15 can generally operate, the X-ray tube 14 may accommodate a barium getter, a nonevaporable getter (NEG), a small ion pump (not shown), or the like that absorbs gas emitted in the X-ray tube 14 in operation. The X-ray tube 14 can be made of a material having a high electrical insulation performance, capable of maintaining a high degree of vacuum, and having high thermal resistance. For example, alumina and heat-resistant glass can be used. As the electron source 15, a filament, an impregnated cathode, a field emission device, or the like can be used.

The target 18 is disposed on the surface of the target substrate 19 adjacent to the electron source 15 so as to face the electron source 15 and is supported by the target substrate 19. Examples of the material of the target 18 include metal, such as tungsten and molybdenum. A plurality of the targets 18 can be arranged linearly or two-dimensionally.

Figures 2, 3:
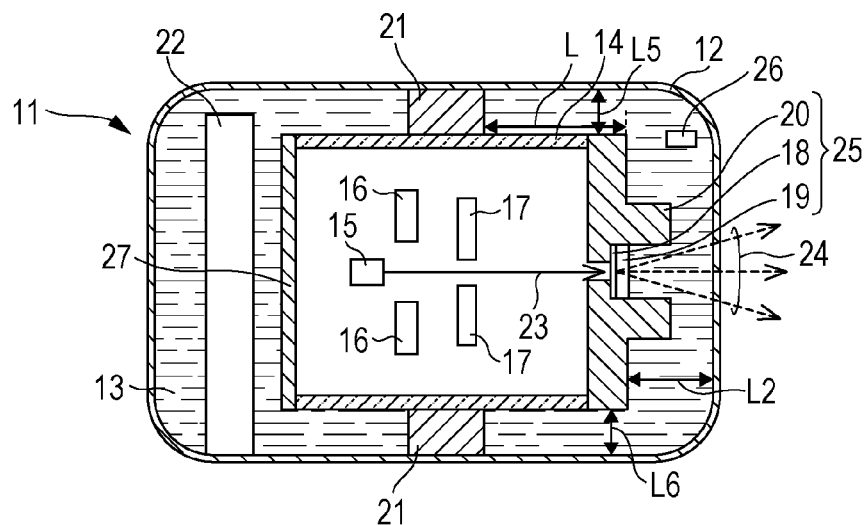
FIG. 2 is a schematic cross-sectional view of another example of the X-ray generator of the first embodiment.
FIG. 3 is a graph showing the relationship between a fixed distance L and the temperature of the insulating liquid.

The target substrate 19 is bonded to the cylindrical shielding member 20 having the function of absorbing X-rays that are generated from the target 18 and are radiated in undesired directions and the function of a thermal diffuser for the target substrate 19 by silver brazing or the like. The shape of the shielding member 20 may be cylindrical, rectangular cylinder, or the like. Electrons emitted from the electron source 15 irradiate the target 18 through an opening of the shielding member 20 adjacent to the electron source 15, and X-rays are generated in the target 18 and are radiated in all directions. The X-rays that have passed through the target substrate 19 are discharged outwards through an opening of the shielding member 20 remote from the electron source 15. In FIG. 1A, the opening of the shielding member 20 remote from the electron source 15 is located outside the target substrate 19. This configuration allows the X-rays radiated outwards from the target 18 to be blocked by the inner wall of the shielding member 20. FIG. 2 illustrates another example of the first embodiment. The components in FIG. 2 are the same as those in FIG. 1A. The configuration in FIG. 2 is the same as that in FIG. 1A except for the shape of the shielding member 20. In FIG. 2, the opening of the shielding member 20 adjacent to the electron source 15 is located inside the target 18. This configuration allows X-rays radiated inwards from the target 18 to be blocked by the inner wall of the shielding member 20. In the first embodiment, since the target substrate 19 that supports the target 18 is bonded to the cylindrical shielding member 20, the heat that is generated in the target 18 when X-rays are generated is transmitted to the target substrate 19 and the shielding member 20 and is then transmitted to the insulating liquid 13 and the X-ray tube 14. The target substrate 19 is not essential. Without the target substrate 19, the target 18 is bonded to the cylindrical shielding member 20 by silver brazing or the like. In this case, the heat generated in the target 18 is transmitted to the insulating liquid 13 and the shielding member 20 and is then transmitted to the X-ray tube 14. The material of the target substrate 19 can have high thermal conductivity and low X-ray absorption performance; for example, SiC, diamond, carbon, thin-film oxygen-free copper, and beryllium. The material of the shielding member 20 can have high X-ray absorption performance; for example, tungsten, molybdenum, oxygen-free copper, lead, tantalum, and other metals.

The holding member 21 is a member for holding the body of the X-ray tube 14. The holding member 21 holds the part of the body substantially equal distance from one end face of the X-ray tube 14 on which the target 18 is provided (hereinafter also referred to as an end face of the target-side wall 25) and the other end face of the X-ray tube 14 at which the target 18 is not provided (hereinafter also referred to as an end face of the electron-source-side wall 27). In FIGS. 1A and 1B, although the X-ray tube 14 is held at two locations of the body by the holding member 21, the X-ray tube 14 has only to be held at at least one location of the body by the holding member 21. In the case where the holding member 21 is at a ground potential as in the first embodiment, the material of the holding member 21 can have electrical conductivity. For example, an electrically conductive material, such as iron, stainless steel, brass, and copper, and an insulating material, such as engineering plastics and ceramics, can be used. The holding member 21 may be made of a material having no electrical conduction performance and is not necessarily be grounded. In the case where both the holding member 21 and the container 12 have thermal conductivity and are in contact with each other, the heat generated in the target 18 is radiated not only from the insulating liquid 13. This allows the heat generated in the target 18 to be transmitted to the X-ray tube 14 and is then transmitted to the holding member 21 and the container 12, and the heat can be radiated also from the container 12.

A first control electrode 16 is a device for extracting electrons generated in the electron source 15. A second control electrode 17 is a device for controlling the focal diameters of the electrons at the target 18. In the case where the first control electrode 16 and the second control electrode 17 are provided as in the first embodiment, an electron flux 23 emitted from the electron source 15 due to an electric field formed by the first control electrode 16 is converged under the potential control of the second control electrode 17. Since the potential of the target 18 is positive with respect to the electron source 15, the electron flux 23 that has passed through the second control electrode 17 is attracted to the target 18 and collides with the target 18 to generate X-rays 24. The ON/OFF of the electron flux 23 is controlled using the voltage of the first control electrode 16. Examples of the material of the first control electrode 16 include stainless steel, molybdenum, and iron.

A power supply circuit 22 is connected to the X-ray tube 14 (the wiring is not shown) and supplies electricity to the electron source 15, the first control electrode 16, the second control electrode 17, and the target 18. In the first embodiment, although the power supply circuit 22 is disposed in the container 12, the power supply circuit 22 may be disposed outside the container 12.

For X-ray imaging of a human organism or the like, the potential of the target 18 is set to be higher than that of the electron source 15 by about +30 kV to 150 kV. The potential difference is accelerating potential difference necessary for the X-rays generated from the target 18 to pass through the human organism, thus advocating to imaging effectively.

The X-ray generator 11 of the first embodiment employs a neutral grounded power system in which, if the potential difference V between the target 18 and the electron source 15 is 20 kV to 160 kV, a potential of +V/2 is applied to the target 18, and a potential of −V/2 is applied to the electron source 15, and grounding is established at the holding member. This is because the container 12 can generally be made compact in consideration of the dielectric breakdown distance of the insulating liquid 13. The first embodiment does not necessarily need employ the neutral grounding; however, because the use of the neutral grounding can decrease the absolute values of the voltage of the target 18 and the voltage of the electron source 15 relative to the ground, the neutral grounding allows the power supply circuit 22 to be made compact as compared with a grounded anode type or the like. Even if the holding member 21 is not grounded at the neutral point but at a location apart from both ends of the X-ray tube 14, the power supply circuit 22 can be made compact as compared with the grounded anode type.

When the thus-configured X-ray generator 11 is operated, heat generation is high at the end of the X-ray tube 14 at which the target 18 is provided. That is, since the heat generated at the target 18 is transmitted to the target substrate 19 and the shielding member 20, heat generation is high at the target-side wall 25. For example, when the X-ray generator 11 is operated at a power output of about 150 W, the maximum temperature of the surface of the shielding member 20 is presumed to be 200 degrees (Celsius) or higher.

Accordingly, to enhance the cooling effect of the convection of the insulating liquid 13, it is necessary to reduce the channel resistance around the target-side wall 25. The inventors have found that separating the holding member 21 a fixed distance L or more from the end face of the target-side wall 25 at the outer circumference thereof ensures a channel for the insulating liquid 13 heated due to the generation of heat in the target 18 to circulate by convection toward the holding member 21, thus enhancing the cooling effect of the convection of the insulating liquid 13. This reduces the channel resistance around the target-side wall 25, thus allowing the heat of the target 18 to be quickly radiated. The fixed distance L is a distance between the holding member 21 and the end face of the target-side wall 25 at the outer periphery thereof in the direction in which the electron source 15 and the target 18 face. The fixed distance L is greater than or equal to 2*Ls, where Ls is the shortest distance of distances between the outer surface of the X-ray tube 14 and the inner surface of the container 12 at the target side of the X-ray tube 14 with respect to the holding member 21 (L1 to L8 in FIGS. 1A and 1B, and L2, L5, and L6 in FIG. 2). The shortest distance Ls can also be referred to as the minimum width of the channel in contact with the outer surface of the X-ray tube 14 at the target side of the X-ray tube 14 with respect to the holding member 21. Assuming that the potential difference V between the potential of the target 18 and the potential of the electron source 15 is 20 kV to 160 kV, the shortest distance Ls can be 1 mm to 20 mm. The fact that setting the fixed distance L twice as large as the shortest distance Ls enhances the cooling effect of the convection of the insulating liquid 13 will be described with reference to FIG. 3.

FIG. 3 is a graph showing the relationship between the fixed distance L and the temperature of the insulating liquid 13 measured by a temperature sensor 26 disposed in the vicinity of the target-side wall 25. As shown in FIG. 3, if the fixed distance L is Ls and 1.5*Ls, the temperature increases with time; however, if the fixed distance L is 2*Ls and 2.5*Ls, the temperature hardly increases after a lapse of a fixed time. This shows that if the fixed distance L is twice or larger than the shortest distance Ls, the insulating liquid 13 circulates by convection smoothly, thus enhancing the cooling effect.

Second Embodiment

Figure 4A:
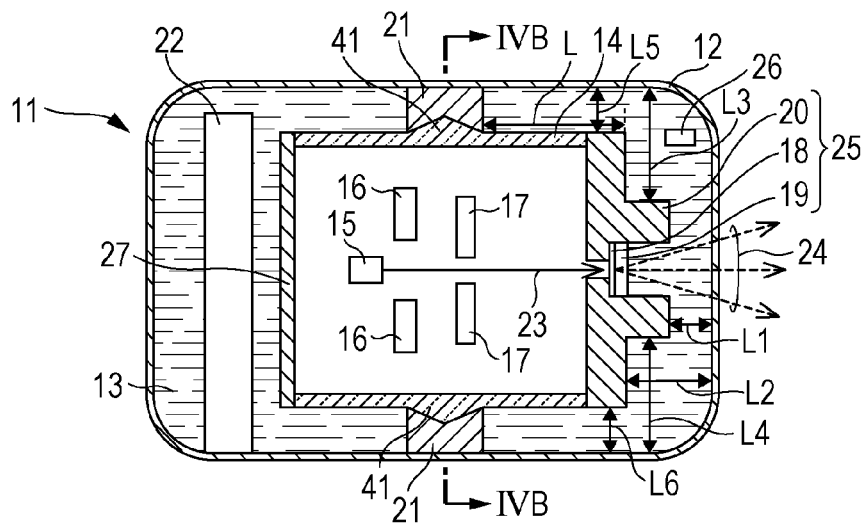
FIG. 4A is a schematic cross-sectional view of an X-ray generator according to a second embodiment of the present invention.
Figure 4B:
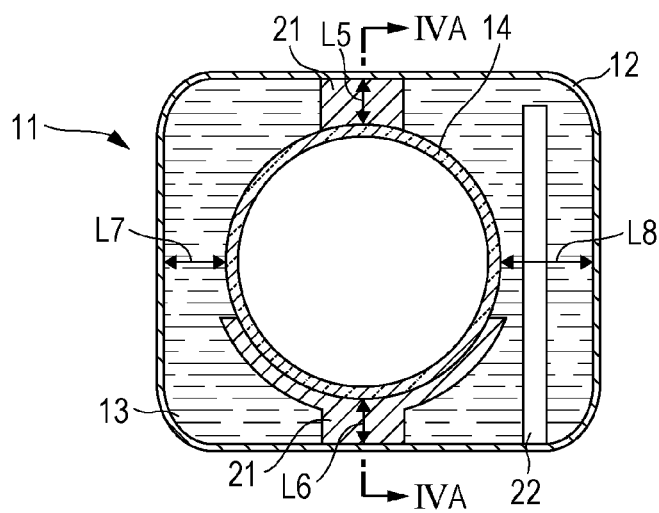
FIG. 4B is a schematic cross-sectional view of the X-ray generator according to the second embodiment.
Figure 4C:
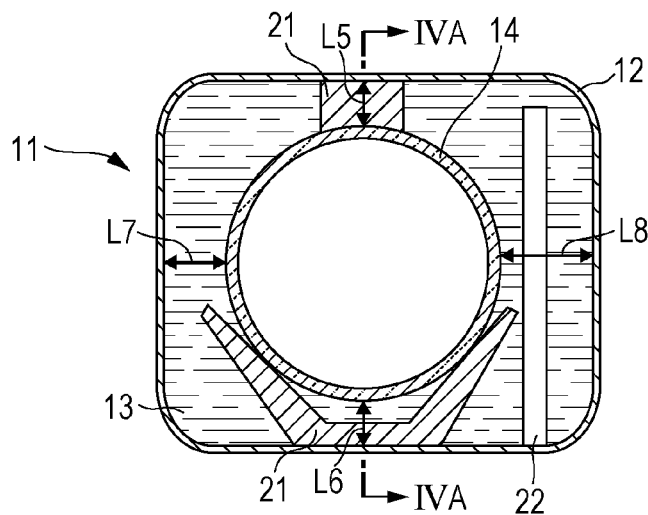
FIG. 4C is a schematic cross-sectional view of the X-ray generator according to the second embodiment.

FIG. 4A is a schematic cross-sectional view of an X-ray generator 11 according to a second embodiment of the present invention, taken along a plane including line IVA-IVA in FIG. 4B. FIG. 4B is a schematic cross-sectional view of the X-ray generator 11 according to the second embodiment, taken along a plane including line IVB-IVB in FIG. 4A. FIG. 4C illustrates an example in which a holding member 21 different from that in FIG. 4B is used.

The X-ray generator 11 of the second embodiment differs from that of the first embodiment in that the X-ray tube 14 and the holding member 21 are fitted together. Since the second embodiment has the same components and configuration as those of the first embodiment except that difference, descriptions of components other than the X-ray tube 14 and the holding member 21 and a description of the configuration of the X-ray generator 11 will be omitted.

The contact portion of the X-ray tube 14 with the holding member 21 has a wedge-shaped protruding portion 41, and the contact portion of the holding member 21 with the X-ray tube 14 has a shape that fits on the protruding portion 41. By fitting them together, the body of the X-ray tube 14 is held. The second embodiment allows the X-ray tube 14 to be held more stably because the X-ray tube 14 and the holding member 21 are fitted together. In FIGS. 4A and 4B, although the X-ray tube 14 is held at two locations of the body by the holding member 21, the X-ray tube 14 has only to be held at at least one location of the body by the holding member 21; as illustrated in FIG. 4C, the X-ray tube 14 may be held at three location of the body by the holding member 21. In the case where the area where the X-ray tube 14 and the holding member 21 are in contact at one of the two location is large, as in FIG. 4B, or in the case where the X-ray tube 14 is held at three locations, as in FIG. 4C, the X-ray tube 14 can be held more stably.

Third Embodiment

Figure 5A:
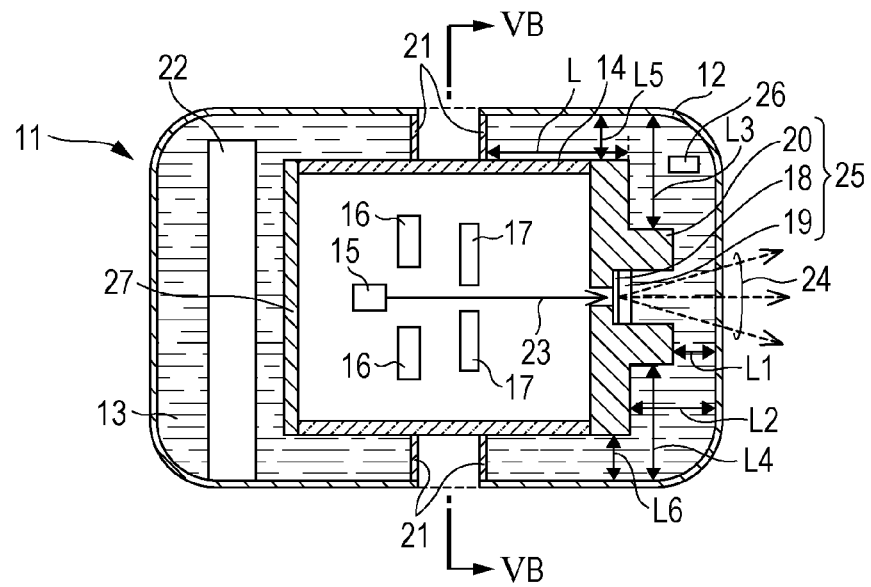
FIG. 5A is a schematic cross-sectional view of an X-ray generator according to a third embodiment of the present invention.
Figure 5B:
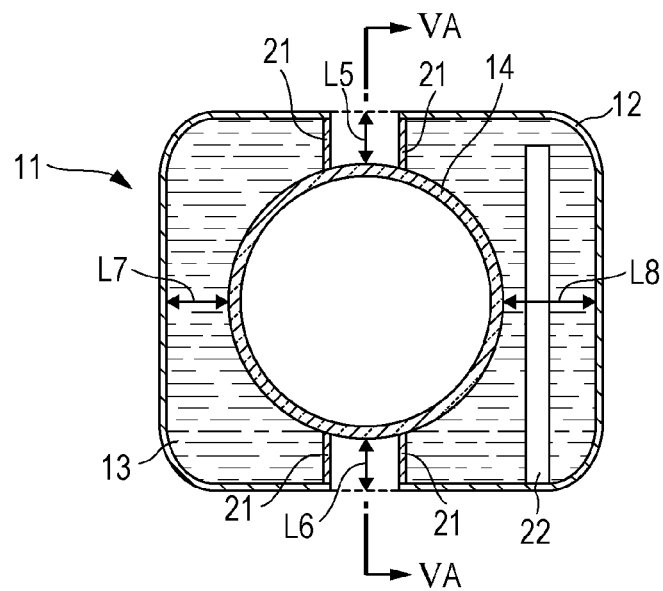
FIG. 5B is a schematic cross-sectional view of the X-ray generator according to the third embodiment.

FIG. 5A is a schematic cross-sectional view of an X-ray generator 11 according to a third embodiment of the present invention, taken along a plane including line VA-VA in FIG. 5B. FIG. 5B is a schematic cross-sectional view of the X-ray generator 11 of the third embodiment, taken along a plane including line VB-VB in FIG. 5A.

The X-ray generator 11 of the third embodiment differs from that of the first embodiment in that the holding member 21 is part of the container 12. Since the second embodiment has the same components and configuration as those of the first embodiment except the difference, descriptions of components other than the container 12 and the holding member 21 and a description of the configuration of the X-ray generator 11 will be omitted.

The holding member 21 is part of the container 12. In FIGS. 5A and 5B, a protruding portion provided at part of the inner surface of the container 12 serves as the holding member 21. For example, a stainless steel or the like having a plate thickness of 0.1 mm to 3 mm can be used as the holding member 21. Thus, the third embodiment does not need to provide the container 12 and the holding member 21 separately. In the third embodiment, since the holding member 21 is part of the container 12, if the container 12 has thermal conductivity, the heat generated in the target 18 is transmitted to the X-ray tube 14, then to the container 12, and can be radiated also from the container 12.

Fourth Embodiment

Figure 6A:
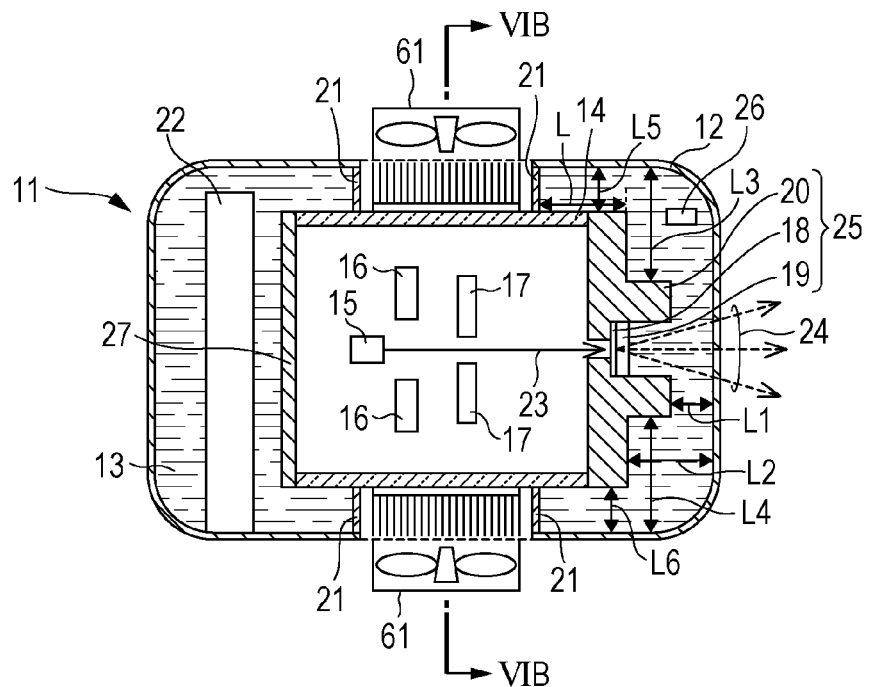
FIG. 6A is a schematic cross-sectional view of an X-ray generator according to a fourth embodiment of the present invention.
Figure 6B:
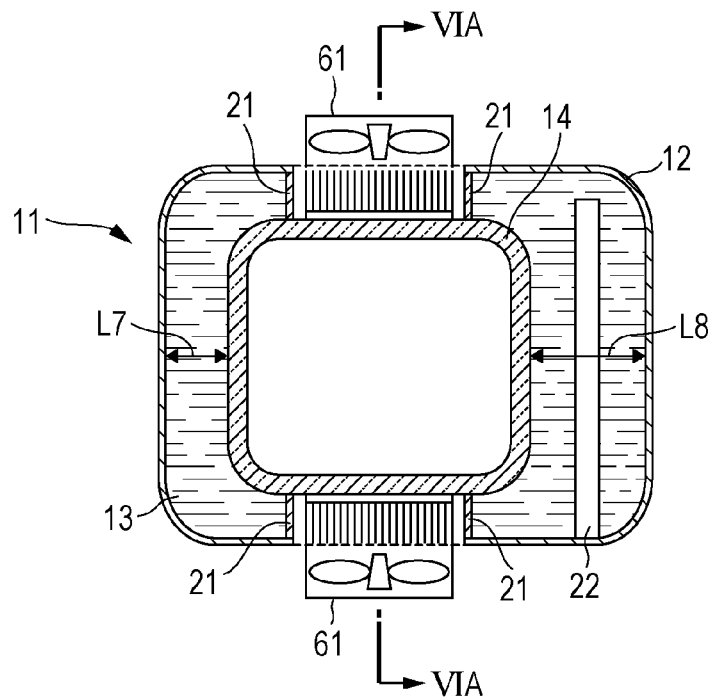
FIG. 6B is a schematic cross-sectional view of the X-ray generator according to the fourth embodiment.
Figure 7A:
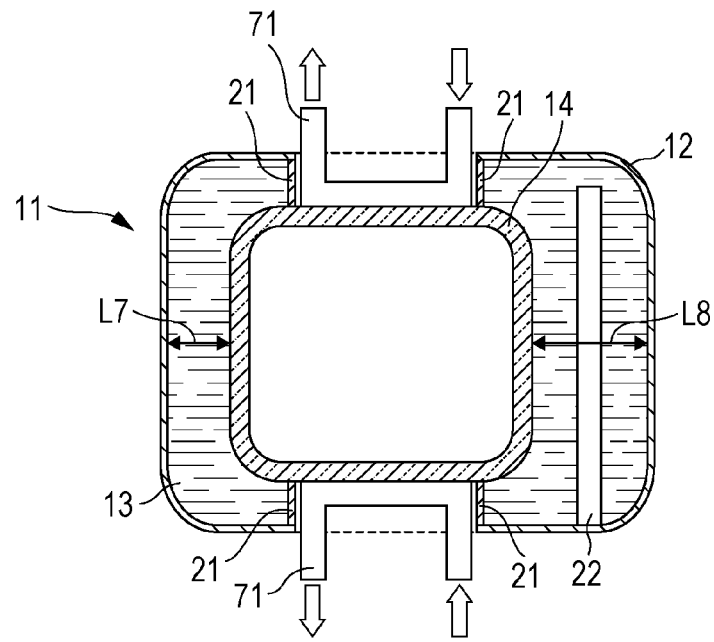
FIG. 7A is a schematic cross-sectional view of another example of the X-ray generator of the fourth embodiment.
Figure 7B:
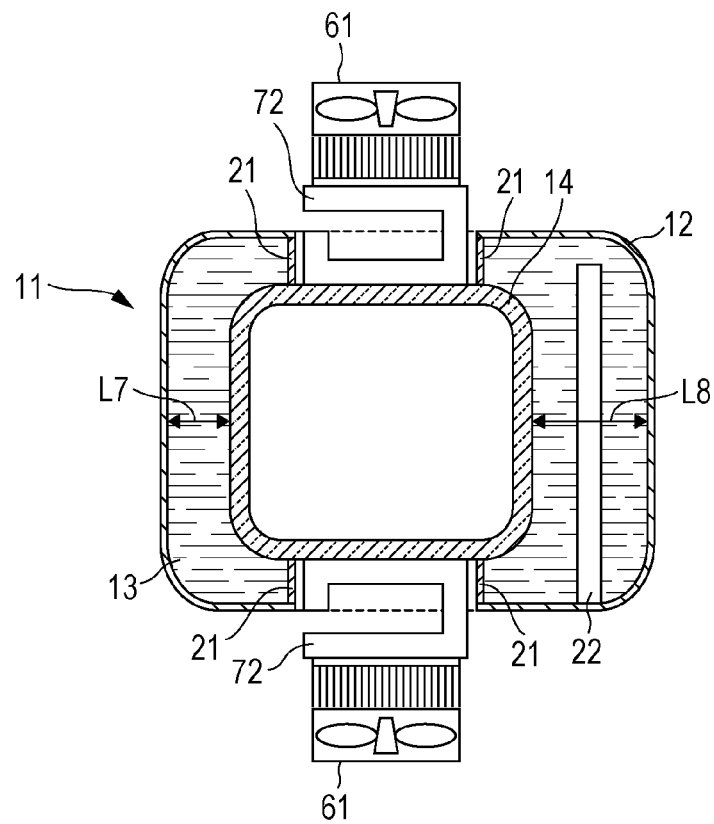
FIG. 7B is a schematic cross-sectional view of another example of the X-ray generator of the fourth embodiment.

FIG. 6A is a schematic cross-sectional view of an X-ray generator 11 of a fourth embodiment of the present invention, taken along a plane including line VIA-VIA in FIG. 6B. FIG. 6B is a schematic cross-sectional view of the X-ray generator 11 of the fourth embodiment, taken along a plane including line VIB-VIB in FIG. 6A. FIGS. 7A and 7B illustrate an example in which a cooler different from that in FIGS. 6A and 6B is used.

The X-ray generator 11 of the fourth embodiment differs from that of the third embodiment in that the cross section of the cylindrical X-ray tube 14 is substantially rectangular and that the container 12 is provided with a cooler. Since the fourth embodiment has the same components and configuration as those of the third embodiment except the difference, descriptions of components other than the X-ray tube 14, the container 12, and the cooler and a description of the configuration of the X-ray generator 11 will be omitted.

Although the cross section of the X-ray tube 14 is substantially rectangular, it may be circular or the like. The container 12 has thermal conductivity and is provided with an air cooling device 61 as a cooler. In FIGS. 6A and 6B, the air cooling device 61 is placed in a protruding portion provided at part of the inner surface of the container 12 serving as the holding member 21. The air cooling device 61 is a combination of a cooling fin and an air cooling fin. Examples of the material of the holding member 21 include a copper having a plate thickness of 0.2 mm to 5 mm. In the fourth embodiment, since the container 12 is provided with the cooler, the container 12 can also be cooled, thus enhancing the performance of cooling the X-ray tube 14. The same effect can be offered also by a liquid cooling device 71, as illustrated in FIG. 7A, and by a combination of a heat pipe 72 and the air cooling device 61, as illustrated in FIG. 7B.

Fifth Embodiment

Figure 8:
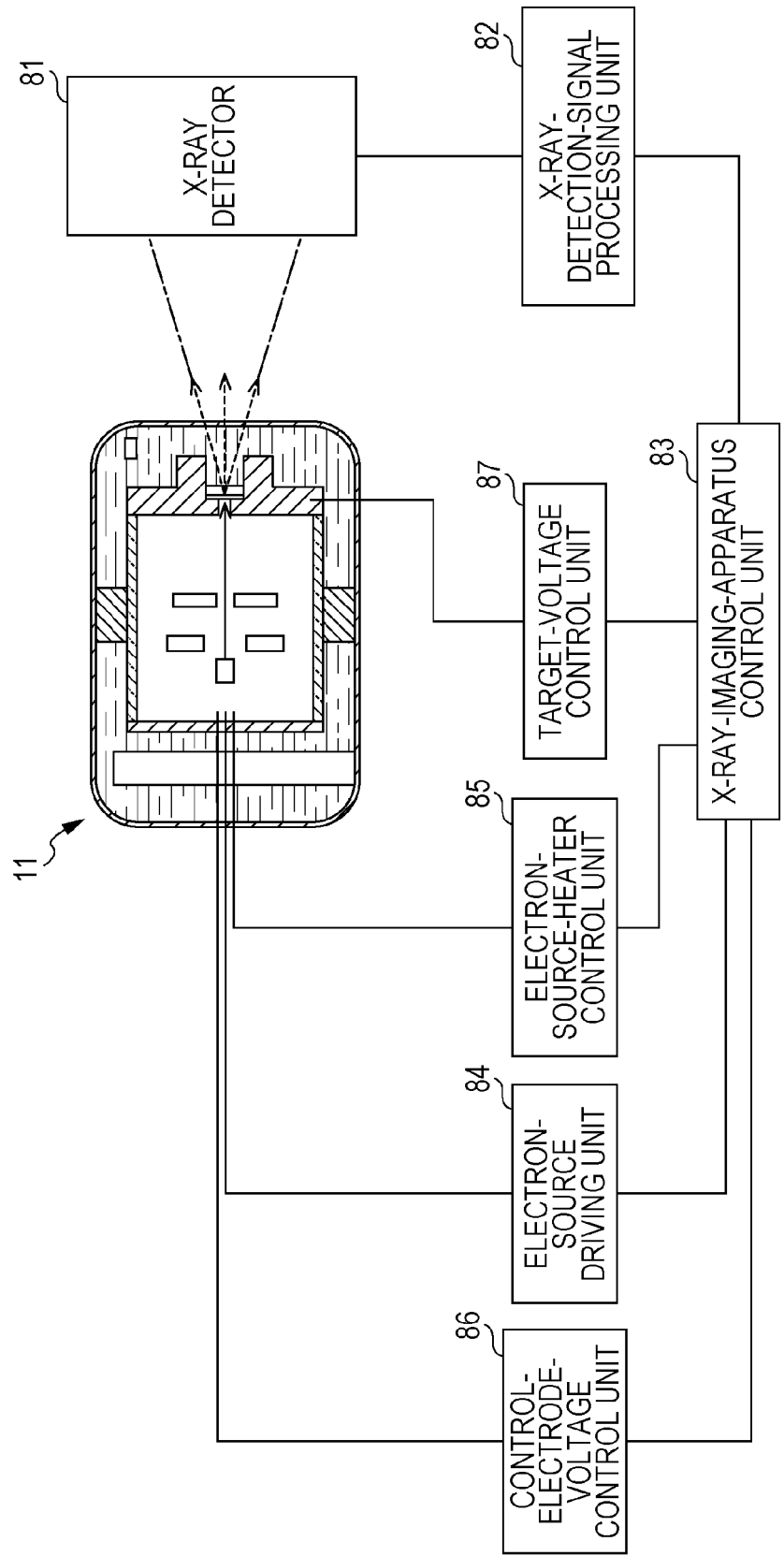
FIG. 8 is a configuration diagram of an X-ray imaging apparatus including the X-ray generator according to one of the embodiments of the present invention.

FIG. 8 is a configuration diagram of an X-ray imaging apparatus of a fifth embodiment of the present invention. One of the X-ray generators 11 according to the first to fourth embodiments is used as the X-ray generator 11.

An X-ray detector 81 is connected to an X-ray-imaging-apparatus control unit 83 via an X-ray-detection-signal processing unit 82. The X-ray-imaging-apparatus control unit 83 controls an electron-source driving unit 84, an electron-source-heater control unit 85, a control-electrode-voltage control unit 86, a target-voltage control unit 87, and the X-ray-detection-signal processing unit 82 cooperatively.

When X-rays are generated by the X-ray generator 11, the X-rays emitted to the atmosphere pass through a subject (not shown) and are detected by the X-ray detector 81, where a radioscopic image of the subject is obtained. The obtained radioscopic image can be displayed on a display (not shown).

Thus, since the fifth embodiment employs an X-ray generator that offers the advantages of the first to fourth embodiments, a reliable X-ray imaging apparatus capable of generating X-rays stably for a long time can be achieved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-088806, filed Apr. 13, 2011, which is hereby incorporated by reference herein in its entirety.

REFERENCE SIGNS LIST

11 X-ray generator
12 Container

13 Insulating liquid
14 X-ray tube
15 Electron source
18 Target
19 Target substrate
21 Holding member
23 Electron flux
24 X-rays
25 Target-side wall of X-ray tube
27 Electron-source-side wall of X-ray tube
61 Air cooling device
71 Liquid cooling device
72 Heat pipe
81 X-ray detector

The invention claimed is:

1. An X-ray generator comprising:
   an X-ray tube including a cylindrical body with two end faces;
   an electron source in the cylindrical body between the two end faces;
   a target arranged at an end face of the cylindrical body so as to face the electron source, the target generating X-rays by irradiation with electrons emitted from the electron source;
   a container in which the X-ray tube is arranged;
   insulating liquid filled between the X-ray tube and the container; and
   a holding member holding the cylindrical body in the container, the holding member forming a channel for the insulating liquid around the X-ray tube,
   wherein a direction in which the electron source and the target face each other is parallel to a cylindrical axis of the cylindrical body, and
   wherein a distance, which is measured parallel to the cylindrical axis, between the holding member and the outer surface of the X-ray tube at the end face where the target is arranged is twice or more as large as a minimum width of the channel.

2. The X-ray generator according to claim 1, wherein the X-ray tube is held by fitting the cylindrical body and the holding member together inside the container.

3. The X-ray generator according to claim 1, wherein both the holding member and the container have thermal conductivity and are in contact with each other.

4. The X-ray generator according to claim 1, wherein the holding member is part of the container.

5. The X-ray generator according to claim 4, wherein the part of the container is a protruding portion at part of the inner surface of the container.

6. The X-ray generator according to claim 1, wherein the container has thermal conductivity.

7. The X-ray generator according to claim 6, wherein the container includes a cooler.

8. The X-ray generator according to claim 1, wherein the holding member has electrical conductivity and is grounded.

9. The X-ray generator according to claim 1, wherein the insulating liquid is electrically insulating oil.

10. An X-ray imaging apparatus comprising the X-ray generator according to claim 1 and an X-ray detector that detects X-rays that is generated from the X-ray generator and that have passed through a subject.

* * * * *